(12) United States Patent
Wills et al.

(10) Patent No.: US 6,717,011 B1
(45) Date of Patent: Apr. 6, 2004

(54) CHIRAL DIAZAPHOSPHOLIDINE LIGANDS

(75) Inventors: Martin Wills, Kenilworth (GB); Simon William Breeden, Tuam (GB)

(73) Assignee: Stylacats Limited, Manchester (GB)

( * ) Notice: Subject to any disclaimer, the term of this patent is extended or adjusted under 35 U.S.C. 154(b) by 0 days.

(21) Appl. No.: 09/914,144

(22) PCT Filed: Feb. 16, 2000

(86) PCT No.: PCT/GB00/00538

§ 371 (c)(1),
(2), (4) Date: Dec. 12, 2001

(87) PCT Pub. No.: WO00/50430

PCT Pub. Date: Aug. 31, 2000

(30) Foreign Application Priority Data

Feb. 23, 1999 (GB) ............................................. 9903973
Jan. 11, 2000 (GB) ............................................. 0000428

(51) Int. Cl.$^7$ ............................................. C07F 9/547
(52) U.S. Cl. ............................. 564/13; 564/12; 556/13
(58) Field of Search ....................... 564/12, 13; 556/13

(56) References Cited

PUBLICATIONS

Brunel et al. (1997), *Tetrahedron Letters*, vol. 38, "Enantioselective Palladium Catalyzed Allylic Substitution with New Chiral Pyridine–Phosphine Ligands": pp. 5971–5974 (1998).

Brunel et al. (1998), *Tetrahedron Letters*, vol. 39 "New Chiral o–Hydroxyphenyl Aromatic Diazaphospholidine Oide. Catalytic Application in Assymetric Addition of Diethylzinc to Aldehydes" : pp. 2961–2964 (1998).

Brunel et al. (1997), *Journal of Organometallic Chemistry*, vol.529, "Use of new chiral tricoordinated phosphorus borane complexes in enantioselective borane reduction of ketones: complexes structure and mechanistic studies" : pp. 285–294.

Burk et al. (1998), *J. Am. Chem. Soc.*, vol. 120, "Highly Regio— and Enantioselective Catalytic Hydrogenation of Enamides in Conjugated Diene Systems: Synthesis and Application of γ,δ—Unsaturated Amino Acids": pp. 657–663 (1998).

(List continued on next page.)

*Primary Examiner*—Jean F. Vollano
(74) *Attorney, Agent, or Firm*—Ohlandt, Greeley, Ruggiero & Perle

(57) ABSTRACT

The application relates to diazaphospholidine compounds of Formula 1 and Formula 2:

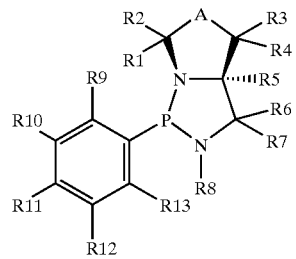

Formula 1

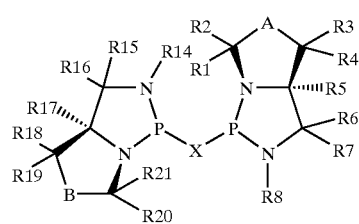

Formula 2 where:
  A and B are independently selected from $C(R_{22}R_{23})$ and $C(R_{22}R_{23})C(R_{24}R_{25})$;
  $R_1$, $R_2$, $R_3$, $R_4$, $R_{18}$, $R_{19}$, $R_{20}$, $R_{21}$, $R_{22}$, $R_{23}$, $R_{24}$ and $R_{25}$ each may not be present and each may be independently selected from H, halide —OH, —$SO_2R_{26}$ (where $R_{26}$ is selected from a group as defined for $R_{22}$, $R_{23}$, $R_{24}$ and $R_{25}$), —SH, —$NO_2$, —$NH_2$, =O, =S, straight chain, branched chain, cyclic, saturated, non-saturated, substituted or non-substituted alkyl, hydroalkyl, carboalkyl, alkoxy, amino, alkenyl, aryl and —$CH_2$ Ar (where Ar is aryl or substituted aryl), preferably containing 1 to 6 carbons, or a silane containing 1 to 6 silicon atoms,
  wherein, where an $R_1$, $R_2$, $R_3$, $R_4$, $R_{18}$, $R_{19}$, $R_{20}$, $R_{21}$, $R_{22}$, $R_{23}$, $R_{24}$ and/or $R_{25}$ group is not present an unsaturated bond is formed;
  $R_5$ and $R_{17}$ are selected from H, —$NH_2$, —OH, halide or a substituted or non-substituted straight or branched chain alkyl or aryl; $R_6$, $R_7$, $R_{15}$ and $R_{16}$ are each independently selected from halide —OH, —$SO_2$, —SH, —$NO_2$, —$NH_2$, straight chain, branched chain, cyclic, saturated, non-saturated, substituted or non-substituted alkyl, carboalkyl, alkoxy, alkenyl, aryl and —$CH_2$ Ar (where Ar is aryl or substituted aryl), or a silane containing 1 to 6 silicon atoms;
  $R_8$ and $R_{14}$ are selected from H, straight, branched, cyclic, saturated, non-saturated, substituted or non-substituted alkyl, carboalkyl, alkoxy, alkenyl, aryl and —$CH_2$ Ar (where Ar is aryl or substituted aryl);
  $R_9$, $R_{10}$, $R_{11}$, $R_{12}$, $R_{13}$ are independently selected from halide —OH, —$SO_2$, —SH, —$NO_2$, —$NH_2$, straight chain, branched chain, cyclic, saturated, non-saturated, substituted or non-substituted alkyl, carboalkyl, alkoxy, amino, alkenyl, aryl and —$CH_2$ Ar (where Ar is aryl or substituted aryl), or a silane containing 1 to 6 silicon atoms; and
  X is a linking group containing 1 to 12 atoms;
or a salt thereof.

These compounds may be used as catalysts for asymmetric catalysts of organic reactions.

33 Claims, No Drawings

OTHER PUBLICATIONS

Burk et al. (1993), *J. Am. Chem. Soc.,* vol. 115, "Preparation and Use of $C_2$–Symmetryc Bus(phospholanes): Production of α—Amino Acid Derivatives via Highly Enentioselective Hydorgenation Reactions": pp. 10125–10138 (1993).

Constantieux et al. (1998), Synlett, "Enantioselective Palladium Catalyzed Allylic Amination Using New Chiral Pyridine–Phosphine Ligands" : pp. 49–50 (1998).

Muchow et al. (1998), *Tetrahedron,* vol. 54, "Pd (0) Catalyzed Assymetric Amination of a Prochiral Bicyclic Allylic Diacetate" : pp. 10435–10448 (1998).

Tye et al. (1997), *Chem. Commun.,* "Synthesis and applications of a new class phosphorus donor ligands for asymmetric catlaysis": pp. 1053–1054 (1997).

CHIRAL DIAZAPHOSPHOLIDINE LIGANDS

This application is a 371 of PCT/GB00/00538 filed Feb. 16, 2000, now WO 00/50430.

The invention relates to chiral diazaphospholidines, to methods for their preparation, and to their use in catalysts for the asymmetric catalysis of organic reactions.

Catalysts for asymmetric transformations are of great value in organic synthesis. The modification of an organometallic system with a suitable enantiomerically pure ligand is perhaps the most effective and efficient means to achieve this. The most popular of the systems reported to date contain ligands based on phosphorus donors, such as phosphines. The combination of ruthenium with the ligand BINAP was reported by Akutagawa S. (Chirality in Industry, Edt. A. N. Collins el al. (1992), J. Wiley & Sons, Chapter 17, pages 325–329).

DuPHOS, 1,2-(phospholano)benzenes have been demonstrated by Burk el al. (J. Am. Chem. Soc. (1993), vol. 115, pages 10125–10138 and (1998), Vol. 120, pages 657–663) and are the subject of U.S. Pat. No. 5,008,457 and U.S. Pat. No. 5,559,267. Such compounds have been found to be commercially useful, especially as hydrogenation catalysts when used in combination with ruthenium or rhodium.

Brunel J. M. et al (Tet. Lett., (1997), Vol. 38, pages 5971–5974) discloses the use of pyridine-phosphine ligands for enantioselective palladium catalysed substitution allylic substitution. The same group have also disclosed the use of diazaoxaphospholidones, Constantieux T. et al (Synlett, (1998), pages 49–50).

Brunel J. M. et al. (Tet. Lett., (1998), Vol. 39, pages 2961–2964) discloses the use of a pentavalent phosphorus system in the form of o-hydroxyphenyl diazaphospholidine oxide. One of the intermediates used to produce such a compound is a hydroxyphenyl diazaphospholidine. However, this later compound was not tested as a catalyst.

Other diazaphospholidines have been disclosed in the article by Tye et al. (Chem. Commun., (1997) pages 1053–1054).

It is an aim of the current invention to provide novel compounds having improved catalytic properties.

It is also an aim of the current invention to identify compounds which are capable of being produced by industrially applicable processes.

Accordingly, a first aspect of the invention provides a chemical compound represented by Formula 1 or Formula 2.

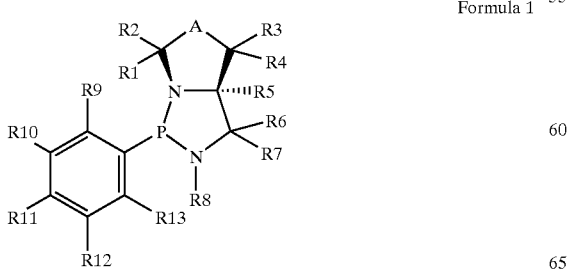

Formula 1

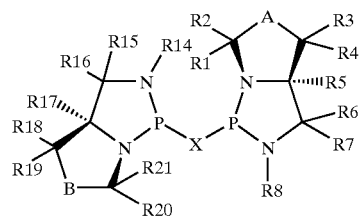

Formula 2

Where:
A and B are independently selected from $C(R_{22}R_{23})$ and $C(R_{22}R_{23})C(R_{24}R_{25})$ especially $CH_2$ or $(CH_2)_2$, preferably A and B are the same; $R_1$, $R_2$, $R_3$, $R_4$, $R_{18}$, $R_{,9}$, $R_{20}$, $R_{21}$, $R_{22}$, $R_{23}$, $R_{24}$ and $R_{25}$ each may or may not be present and each may be independently selected from H, halide —OH, —$SO_2R_{26}$ (where $R_{26}$ is selected from a group as defined for $R_{22}$, $R_{23}$, $R_{24}$ and $R_{25}$), —SH, —$NO_2$, —$NH_2$, =O, =S, straight chain, branched chain, cyclic, saturated, non-saturated, substituted or non-substituted alkyl, hydroalkyl, carboalkyl, alkoxy, amino, alkenyl, aryl and $CH_2$ Ar (where Ar is aryl or substituted aryl), preferably containing 1 to 6 carbons, more preferably 1 or 2 carbons, or a silane containing 1 to 6 silicon atoms; wherein, where an $R_1$, $R_2$, $R_3$, $R_4$, $R_{18}$, $R_{19}$, $R_{20}$, $R_{21}$, $R_{22}$, $R_{23}$, $R_{24}$ and/or $R_{25}$ group is not present an unsaturated bond is formed; preferably $R_1$, $R_2$, $R_3$ and $R_4$ are identical to $R_{21}$, $R_{20}$, $R_{19}$ and $R_{18}$ respectively; Preferably $R_5$ and $R_{17}$ are selected from H, —$NH_2$, —OH substituted or non-substituted straight or branched chain alkyl or aryl, and halide, preferably the alkyl or aryl is a $C_1$, to $C_6$ alkyl or aryl, more preferably $R_5$ and $R_{17}$ being both the same. $R_5$ and $R_{17}$ may especially be H; $R_6$, $R_7$, $R_{15}$ and $R_{16}$ are each independently selected from halide —OH, —$SO_2R_{26}$, —SH, —$NO_2$, —$NH_2$, straight chain, branched chain, cyclic, saturated, non-saturated, substituted or non-substituted alkyl, carboalkyl, alkoxy, alkenyl, aryl and $CH_2$ Ar (where Ar is aryl or substituted aryl), preferably containing 1 to 6 carbons, more preferably 1 or 2 carbons, or a silane containing 1 to 6 silicon atoms, wherein preferably $R_6$ and $R_7$ are identical to $R_{15}$ and $R_{16}$ respectively; $R_8$ and $R_{14}$ are selected from H, straight, branched, cyclic, saturated, non-saturated, substituted or non-substituted alkyl, carboalkyl, alkoxy, alkenyl, aryl and $CH_2$ Ar (where Ar is aryl or substituted aryl), preferably containing 1 to 6 carbons, phenyl or substituted phenyl being especially preferred, $R_8$ and $R_{14}$ being preferably identical; $R_9$, $R_{10}$, $R_{11}$, $R_{12}$, $R_{13}$ are independently selected from halide —OH, —$SO_2R_{26}$, —SH, —$NO_2$, —$NH_2$, straight chain, branched chain, cyclic, saturated, non-saturated, substituted or non-substituted alkyl, carboalkyl, alkoxy, amino, alkenyl, aryl and $CH_2$ Ar (where Ar is aryl or substituted aryl), preferably containing 1 to 6 carbons, more preferably 1 or 2 carbons, or a silane, containing 1 to 6 silicon atoms, most preferably $R_9$ is OMe, $R_{10}$, $R_{11}$, $R_{12}$ and $R_{13}$ preferably being each H; X is a linking group containing 1 to 12 atoms, preferably the linking group being selected from —S—S—, —O—O—, straight chain, branched chain, cyclic, substituted or non-substituted alkyl, carboalkyl, alkoxy, alkenyl and aryl, preferably X containing 1 to 6 carbon atoms, most preferably X is a disubstituted aromatic moiety.

Preferably the invention provides compounds according to the first aspect of the invention with the provisos that together A is not $CH_2$; $R_1$, $R_2$, $R_3$, $R_4$, $R_5$, $R_6$, $R_7$, $R_{10}$, $R_{11}$, $R_{12}$ and $R_{13}$ are not each H, $R_8$ is not Ph; and $R_9$ is not —OMe.

The compounds of the invention contain a chiral environment which is both rigid in structure and which, when complexed to a transition metal to form a catalyst, is located in close proximity to the metal reaction centre. Both of these features appear to account for the high asymmetric inductions observed by the inventors.

Having a —OMe group at position $R_9$ has been found to improve the selectivity of the compounds when used as catalysts. Furthermore, an aromatic group at $R_8$ in the case of compounds of Formula 1 and $R_8$ and $R_{14}$ in the case of Formula 2, has also been found to improve the selectivity of the compounds when used as catalysts.

Preferably the compound, according to Formula 1 the first aspect of the invention, has a formula according to Formula 3;

Formula 3

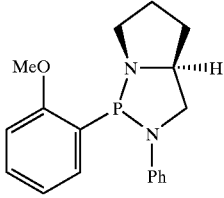

With respect to Formula 2, the groups on each side of linking group X are preferably identical, to facilitate easier production of the ligand compound.

Preferably the compounds of Formula 2 of the invention have a general Formula 4:

Formula 4

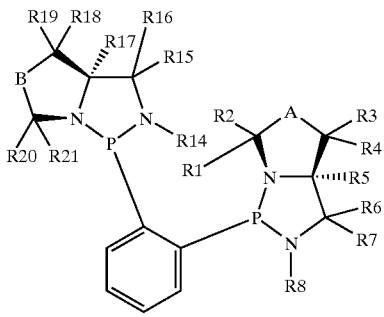

More preferably the compounds of this aspect of the invention have a formula according to Formula 5;

Formula 5

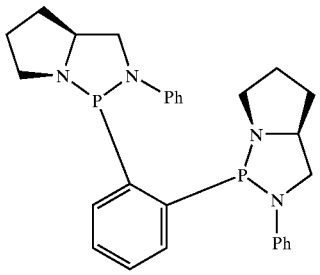

In use the compounds of the invention are chelated with at least one metal ion to form a catalytic compound. Accordingly a second aspect of the invention provides a catalytic compound comprising a compound according to the first aspect of the invention chelated to at least one transition metal ion.

Preferably the transition metal ion is selected from palladium, ruthenium, rhodium, tungsten, nickel, platinum, copper, cobalt, zinc and molybdenum. The complexation methods used are those known in the art.

A third aspect of the invention provides a chemical formulation or composition, comprising either a compound according to the first aspect of the invention or a catalyst according to the second aspect of the invention.

A fourth aspect of the invention provides a process for carrying out a chemical reaction comprising reacting reactants in the presence of a catalyst according to the second aspect of the invention. Preferably the chemical reaction is an organic asymmetric catalysis reaction.

The compounds and catalysts of the invention allow high levels of enantiomeric excess (e.e.) and percentage yield to be produced. Enantiomeric excess is defined as (% major enantiomer)–(% minor enantiomer). A compound of high enantiomeric excess preferably exhibits an enantiomeric excess of >80%, especially >90%. A compound of very high e.e. exhibits an e.e. of >95%.

Preferably the asymmetric catalysis reaction is asymmetric hydrogenation. This technique is demonstrated in, for example, the papers by Burk et al (1993, 1998—Supra). A hydrogenation process comprising providing a substrate containing a reducible double bond dissolved in an inert solvent together with a catalyst according to the second aspect of the invention under a pressure of hydrogen of at least 1 atmosphere, stirring the reaction to completion, and isolating the product.

Preferably the metal in the catalyst is rhodium.

The asymmetric catalyst reaction may be allylic substitution. This is shown in, for example, Constantieux T. et al. (Synlett, (1998), page 49), Hayashi et al. (J. Am. Chem. Soc., (1994), Vol. 116, pages 775–776) and O'Donnell M. J. et al. (J. Org. Chem., (1997), Vol. 62, pages 3962–3975). Accordingly, the invention provides a process for allylic substitution comprising, providing solution of a substrate containing an appropriate allylic leaving group dissolved in an inert solvent, together with a catalyst according to the second aspect of the invention (preferably with palladium) and a co-reagent (preferably a malonate or an amine), and stirring for a period of time until reaction is deemed to be complete and then stopping the reaction prior to isolating the product.

Asymmetric hydroformylation, hydrovinylation and copolymerisation may also be carried out by methods known in the art. Accordingly the invention provides a process for asymmetric hydroformylation comprising providing a solution of a substrate containing an appropriate double bond dissolved in an inert solvent together with a catalyst according to the second aspect (preferably with rhodium) under an appropriate pressure of carbon monoxide and hydrogen, the solution being stirred for a period of time until reaction is deemed to be complete, and it is then stopped and the product isolated. Based on Nozaki el al., *J. Org. Chem.*, 1997, 62, 4285.

A further aspect provides a process for asymmetric hydrovinylation comprising providing a solution of a substrate containing an appropriate double bond dissolved in an inert solvent together with a catalyst according to the second aspect of the invention (preferably with nickel) under an appropriate pressure of ethene, the solution being stirred for a period of time until reaction is deemed to be complete and is then stopped and the product isolated. Based on Rajanbabu et al. *J. Am. Chem. Soc.* 1998, 120, page 459.

A further aspect of the invention provides a process for asymmetric copolymerisation comprising providing a solution of a substrate containing an appropriate double bond dissolved in an inert solvent together with a catalyst according to the second aspect of the invention (preferably with palladium) under an appropriate pressure of carbon monoxide and propene, the solution being stirred for a period of time until reaction is deemed to be complete and it is then stopped and the product isolated. Based on Z. Zhang and A. Sen, *J. Am. Chem. Soc.*, 1995, 117, 4455.

Conjugate addition reactions may also be carried out using the catalysts of the invention. Such reactions are described in, for example, Feringa et al. (Angew. Chem. Int. Ed. Engl., (1997), Vol. 36, page 2620). The invention therefore provides an asymetric conjugation addition process comprising providing a solution of a copper(II) salt together with a catalyst according to a second aspect of the invention stirring in an inert solvent under a nitrogen atmosphere, the substrate containing a suitable double bond and an appropriate source of alkyl group (preferably diethylzinc) is then added and the mixture stirred until the reaction is deemed to be complete at which point the product is isolated.

Alternatively, the catalysts of the invention may be used for asymmetric hydrosilylation. Such processes are described in Hayashi el al. Tet. Lett. (1996), Vol. 37, page 4169). The invention provides a process for asymmetric hydrosilylation comprising providing a solution of an appropriate substrate containing a reactive double bond, stirring with a complex of a catalyst according to the second aspect of the invention (preferably with palladium or rhodium) and a silyl-based reducing agent (preferably $H_3SiCl$ or $Ph_2SiH_2$) in an inert solvent under a nitrogen atmosphere until the reaction is deemed to be complete as which point the product is isolated.

The invention also includes products having high levels of e.e. obtainable by the processes according to the fourth aspect of the invention.

A fifth aspect of the invention provides a process for the production of a compound according to Formula 1, comprising the steps of:

a) providing a compound of Formula 6:

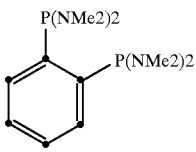

Formula 6 where: $R_9$–$R_{13}$ are as previously defined.

b) mixing the compound of Formula 6 with a compound of Formula 7:

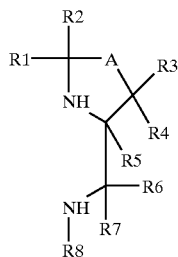

Formula 7 where: $R_1$–$R_8$, and A, are as previously defined; and c) heating the mixture to form a compound of Formula 1.

Preferably the mixture in step c) is refluxed. The heating step c) may be carried out under nitrogen. The components in step b) may be mixed in an organic solvent such as toluene.

Preferably the compound of Formula 6 and the compound of Formula 7 are added in substantially equimolar concentrations.

A sixth aspect of the invention provides a process for the production of a compound according to Formula 2, comprising the steps of:

a) providing a compound having a formula X (P(NMe$_2$)$_2$)$_2$ where X is as previously defined;

b) mixing with a compound of Formula 7 as defined above; and c) heating.

Preferably the component in step a) has Formula 8:

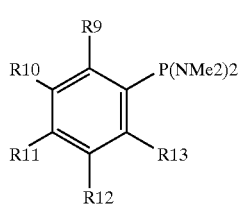

Formula 8

Preferably step c) is carried out by refluxing and may, preferably be carried out under nitrogen. An organic solvent, such as toluene may be used in step b).

Preferably approximately 2 moles of compound of Formula 7 are added to each mole of compound 8.

This process is relatively easy and cost efficient compared with some prior art processes.

The invention will now be described by way of example only.

EXAMPLE 1

Preparation of a Compound of Formula 3

To a stirred solution of (S)-2-(phenylaminomethyl) pyrrolidine (ref. S. Iriuchijima, *Synthesis*, 1978, 684) (1.96 g. 11.12 mmol) in dry degassed toluene (10 ml) was added a solution of 2-anisyl-(bisdimethylamino)-phosphine (ref. G. Buono, H. Arzoumanian, M. Choukard and J-F. Petrignani, *Organometallics*, 1988, 59) (2.5253 g. 11.12 mmol) in dry degassed toluene (15 ml) and the resulting solution refluxed for 42 hours under a positive stream of nitrogen. The solvent was then removed in vacuo to yield a pale yellow solid which was recrystallised from dry degassed toluene (10 ml) to yield Formula 3 as colourless crystals (2.39 g, 69%); mp 154–156° C.; $[\alpha]_D$–493.2 (c 0.5, CHCl$_3$); $^1$H NMR, 400 MHz (C$_6$D$_6$) δ 1.20–1.29 (m, 1H, CH$_2$), 1.42–1.49 (m, 2H, CH$_2$), 1.54–1.63 (m, 1H, CH$_2$), 2.75–2.81 (m, 1H, CH$_2$), 3.09–3.21 (m, 2H, CH$_2$), 3.28 (s, 3H, CH$_3$), 3.29–3.38 (m, 1H, CH$_2$), 3.72–3.84 (m, 1H, CH), 6.48 (dd, J 3.9 and 8.1 Hz, 1H, CH), 6.76–6.84 (m, 2H CH and CH), 6.98–7.04 (m, 2H CH and CH), 7.08–7.13 (m, 1H, CH), 7.16–7.23 (m, 2H, CH and CH), 7.43 (ddd, J 1.8, 3.9 and 7.4 Hz, 1H, CH); $^{31}$P NMR (C$_6$D$_6$) δ 95.0; $^{13}$C NMR, 100 MHz (C$_6$D$_6$) δ 26.13 (d,J$_{C-P}$ 6.2 Hz, CH$_2$), 31.30 (CH$_2$), 52.56 (d, J$_{C-P}$ 30.0 Hz, CH$_2$), 53.31 (d, J$_{C-P}$ 5.2 Hz, CH$_2$), 54.95 (CH$_3$), 64.48 (d, J$_{C-P}$ 8.6 Hz, CH), 110.77 (CH), 115.91 (d, J$_{C-P}$ 12.9 Hz, CH), 117.95 (d, J$_{C-P}$ 1.4 Hz, CH), 120.54 (CH), 129.21 (d,J$_{C-P}$ 1.0 Hz, CH), 130.58 (CH), 131.03 (d, J$_{C-P}$ 3.3 Hz, CH), 147.63 (C), 147.86 (C), 161.90 (d, J$_{C-P}$ 15.3 Hz, CH); m/z (EI) 312 (M$^+$, 43%), 205 (92), 136 (26), 83 (100), 70 (93); Anal. Calcd for C$_{18}$H$_{21}$N$_2$OP; C, 69.2; H, 6.77; N, 8.97. Found; C, 69.28/69.03; H, 6.75/6.73; N, 8.95/8.92.

EXAMPLE 2

Preparation of a Compound of Formula 5

To a stirred solution of (S)-2-(phenylaminomethyl) pyrrolidine (ref. S. Iriuchijima, *Synthesis*, 1978, 684) (3.99 g, 22.7 mmol) in dry degassed toluene (10 ml) was added a solution of 1,2-bis[bisdimethylamino)-phosphine]benzene (ref. K. Drewelies and H. P. Latascha, *Angew. Chem. Int. Ed. Engl.*, 1982, 21, 638) (3.5668 g, 11.3 mmol) in dry degassed toluene (20 ml), and the residue washed in with dry degassed toluene (2×10 ml). The resulting solution was refluxed for 72 hours under a positive stream of nitrogen. The solvent was then removed in vacuo to yield a pale yellow solid which was recrystallised from dry, degassed toluene (20 ml) to yield the product Formula 5 as colourless crystals (4.1522 g, 76%); mp 172–174° C.; [α]$_D$ –674.2 (c 0.5, CHCl$_3$; $^1$H NMR, 400 MHz (C$_6$D$_6$) δ 1.27–1.38 (m, 2H, CH$_2$), 1.41–1.62 (m, 4H, CH$_2$), 1.63–1.78 (m, 2H, CH$_2$), (br.t, J 8.6 Hz, 2H, CH$_2$), 3.05–3.19 (m, 4H, CH$_2$), 3.42–3.55 (m, 2H, CH$_2$), 3.71 (ddd J 2.0, 7.9 and 14.8 Hz, 2H, CH), 6.81 (br.t, J 7.2 Hz, 2H, CH), 6.90 (dt, J 7.2 and 2.0 Hz, 2H, CH), 7.08 (br.d, J 8.1 Hz, 4H, CH), 7.23 (br.t, J 8.0 Hz, 4H, CH), 7.39 (quintet, 2H, CH); $^{31}$P NMR (C$_6$D$_6$) δ 101.85; $_{13}$C NMR, 100 MHz (C$_6$D$_6$) δ 25.95 (d, J$_{C-P}$ 2.3 Hz, CH$_2$), 31.15 (CH$_2$), 52.45 (d, J$_{C-P}$ 14.1 Hz, CH$_2$), 54.56 (d, J$_{C-P}$ 2.0 Hz, CH$_2$), 64.32 (d, J$_{C-P}$ 4.6 Hz, CH), 115.33 (d, J$_{C-P}$ 6.9 Hz, CH), 118.02 (CH), 129.30 (CH), 126.90 (CH), 129.75 (t, J$_{C-P}$ 6.0 Hz, CH), 147.60 (d, J$_{C-P}$ 9.2 Hz, C), 148.32 (d, J$_{C-P}$ 7.8 Hz, C); m/z (EI) 487 (M+H$^+$, 38%), 486 (M$^+$, 100), 403 (36), 312 (73), 149 (44); Anal. Calcd for C$_{28}$H$_{32}$N$_4$P$_2$ (+0.5 C$_7$H8,1/2 toluene of crystallisation); C, 71.04; H, 6.81; N, 10.52. Found; C, 71.00/71.01; H, 6.79/6.81; N, 10.54/10.53.

EXAMPLE 3

Allylic Substitution Reaction With Dimethylmalonate

To a solution of ligand of Formula 3 (24.6 mg, 0.079 mmol) in dry degassed dichloromethane (1.0 ml) was added tris(dibenzylidineacetone)dipalladium(0) (18.1 mg, 0.02 mmol) and the resulting solution stirred for 15 min. during which time the colour changed from purple to orange. 1,3-Diphenyl-3-acetoxy-1-propene, Formula 9 (200 mg, 0.79 mmol) was then added as a solution in dry degassed dichloromethane (1.0 ml), followed by dimethylmalonate (115 mg, 0.1 ml, 0.87 mmol), N,O-bis(trimethylsilyl)-acetamide (176 mg, 0.22 ml, 0.87 mmol) and sodium acetate (1 mg). After 3 hours the solution was diluted with diethyl ether (10 ml) and quenched by the addition of saturated ammonium chloride solution (10 ml). The aqueous phase was extracted with diethyl ether (3×10 ml) and the combined organics dried over magnesium sulfate, filtered and the solvent removed in vacuo to yield an orange oil. Purification by chromatography on silica eluting with 20% ethyl acetate/hexane gave the product of Formula 10 as a clear oil that solidifies on standing (190.2 mg, 74%); $^1$H NMR, 400 MHz (CDCl$_3$) δ 3.52 (s, 3H, CH$_3$), 3.70 (s, 3H, CH$_3$) 3.95 (d, J 10.9 Hz, 1H, CH), 4.26 (dd, J 10.9 and 8.4 Hz, 1H, CH), 6.32 (dd, J 15.8 and 8.4 Hz, 1H, CH), 6.47 (d, J 15.8 Hz, 1H, CH), 7.17–7.34 (m, 10H, aromatics); $^{13}$C NMR, 100 MHz (CDCl$_3$) δ 49.13 (CH), 52.37 and 52.54 (CH$_3$), 57.58 (CH), 126.32, 127.11, 127.52, 128.10, 128.42, 128.66, 129.07, 131.77, 136.77, 140.12 (aromatics and alkene), 167.71 (C=O), 168.13 (C=O); m/z (CI) 324 (M$^+$, 19%), 292 (16), 263 (14), 193 (100), 83 (54). Enantiomeric Excess was determined to be 83% (S) by chiral shift NMR using (+)-Eu(hfc)$_3$. Substrate (Formula 10) (20.0 mg) was dissolved in 1.0 ml CDCl$_3$, and (+)-Eu(hfc)$_3$ (36.8 mg, 0.5 equiv.) added. The solution was shaken for a few seconds during which time a bright yellow solution formed. NMR analysis of this sample (400 MHz) gave 4 singlets in the region of 4.0 ppm. The ratio of the signal at 4.24 ppm to the signal at 4.13 ppm is a measure of the enantiomeric excess, with the signal at 4.13 ppm being the major peak corresponding to the S-enantiomer in this system. All the above data agrees with literature values (ref. G. Brenchley, M. Fedouloff, M. F. Mahon, K. C. Molloy and M. Wills, *Tetrahedron*, 1995, 51, 10581).

Formula 9

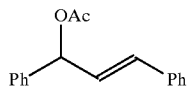

Formula 10

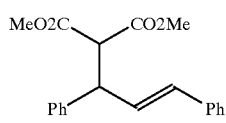

This was repeated with a compound of Formula 5 and produced a product of 96% e.e.

EXAMPLE 4

Allylic Substitution Reaction With Benzylamine (Formula 11)

To a solution of benzylamine (85.7 mg, 0.8 mmol) in dry THF (4 ml) was added sodium hydride (32 mg of a 60% dispersion in mineral oil, 0.8 mmol). After 2 hours the solvent was removed in vacuo and the sodium salt resuspended in dry degassed dichloromethane (2.0 ml). Meanwhile, to a solution of Formula 3 (12.5 mg, 0.04 mmol) in dry degassed dichloromethane (1.0 ml) was added tris (dibenzylidineacetone)dipalladium(0) (9.2 mg, 0.01 mmol) and the resulting solution stirred for 15 min, during which time the colour changed from purple to orange. 1,3-Diphenyl-3-acetoxy-1-propene (Formula 9) (100.8 mg, 0.4 mmol) was then added as a solution in dry degassed dichloromethane (1.0 ml), followed by the suspension of the sodium salt of benzylamine as prepared above. After 48 hours the solution was diluted with diethyl ether (10 ml) and quenched by the addition of saturated ammonium chloride solution (10 ml). The aqueous phase was extracted with diethyl ether (3×10 ml) and the combined organics dried over magnesium sulfate, filtered and the solvent removed in vacuo to yield a yellow oil. Purification by chromatography on silica eluting with 20% ethyl acetate/hexane gave the product (Formula 11) as a clear oil (96.4 mg, 81%); $^1$H NMR, 400 MHz (CDCl$_3$) δ 1.75 (br.s, 1H, NH), 3.77 (AB, J 13.4 Hz, 2H, CH$_2$), 4.38 (d, J 7.3 Hz, 1H, CH), 6.29 (dd, J 15.8 and 7.4 Hz, 1H, CH), 6.57 (d, J 15.8 Hz, 1H, CH), 7.14–7.45 (m, 10H, aromatics): $^{13}$C NMR, 100 MHz (CDCl$_3$) δ 51.36 (CH$_2$) 64.55 (HC), 126.38, 126.89, 127.26, 127.35, 127.41, 128.13, 128.38, 128.47, 128.58, 130.31, 132.60, 136.93, 140.40, 142.87 (aromatics and alkene); m/z (CI) 299 (M$^+$, 28%), 208 (32), 193 (100), 91 (14). Enantiomeric excess was determined to be 95% (R) by chiral HPLC using a Chiralcel OD column, 200:1:0.2 hexane:isopropanol:diethylamine, 0.5 ml/min, 254 nm, t$_r$ for (R) isomer=41.43, t$_r$ for (S) isomer=47.11. All the above data agrees with literature values (ref. P. Von Matt, 0. Loiseleur, G Koch, A. Pfaltz, C. Lefeber, T. Feucht and G. Helmchen, *Tetrahedron Asymmetry*, 1994, 5, 573).

Formula 11

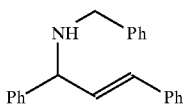

The catalysts of the invention may be used for other reactions. Typical conditions are as follows:

Asymmetric Hydrogenation

The ESPHOS diphosphine (Formula 5) and SEMI-ESPHOS monodentate phosphine (Formula 3) were tested under a variety of conditions for their ability to effect the asymmetric hydroiformylation of vinyl acetate and styrene. The results are summarised in Table 1.

The reactions were carried out in a mini-autoclave fitted with a system for substrate or catalyst injection and for measuring kinetics at constant pressure. The ligand, [Rh(CO)$_2$(acac)] and toluene solvent were placed in the autoclave and flushed with CO/H$_2$ before pressurising to several bars below the operating pressure. The mixture was heated with stirring to the desired reaction temperature. The substrate was then introduced via the substrate injection facility and the pressure raised to the desired reaction pressure. It took ca 90 seconds to stabilise the reaction conditions after the substrate injection. The pressure in the ballast vessel attached to the reaction vessel via a mass flow controller, which metered in gas to keep the constant pressure in the reactor, was monitored electronically with time. At the end of the reaction, the stirrer was stopped and the reactor cooled by plunging it into cold water. The liquid products were analysed by GC-FID (quantitative) and GC-MS (qualitative) using a chiral capillary column.

Generally speaking, heating the rhodium source and phosphine ligand under CO/H$_2$ lead to the rapid formation of the catalytically active species so that any reaction started immediately the substrate was introduced, although for low pressure and temperature reactions formation of the active species took longer leading to an induction period. There were two types of kinetic behaviour normally observed—first order in substrate or zero order in substrate and the order with respect to substrate gives information on the alkene binding step:

where L$_2$ is two monodentate or one bidentate ligand and S is the substrate. If this equlibrium does not lie totally to the right (which is usually the case), the reaction will be first order in substrate; if it does lie totally to the right it will be zero order. A complication occurred in that at low CO/H$_2$ pressures (8 or 10 bar of CO/H$_2$), gas diffusion into the liquid phase became rate determining. When this occurred the kinetics could give a misleading appearance of 0 order dependence on substrate concentration as well as misleading product distributions. There is a simple explanation for the change in product distribution observed when the reactant solution is 'starved' of CO during Rh catalysed hydroformylation reactions. The first step involves coordination of styrene followed by reversible rhodium bound H transfer to give both the straight and branched chain Rh-alkyl species, which because of the reversibility of the hydrogen transfer, are in equilibrium.

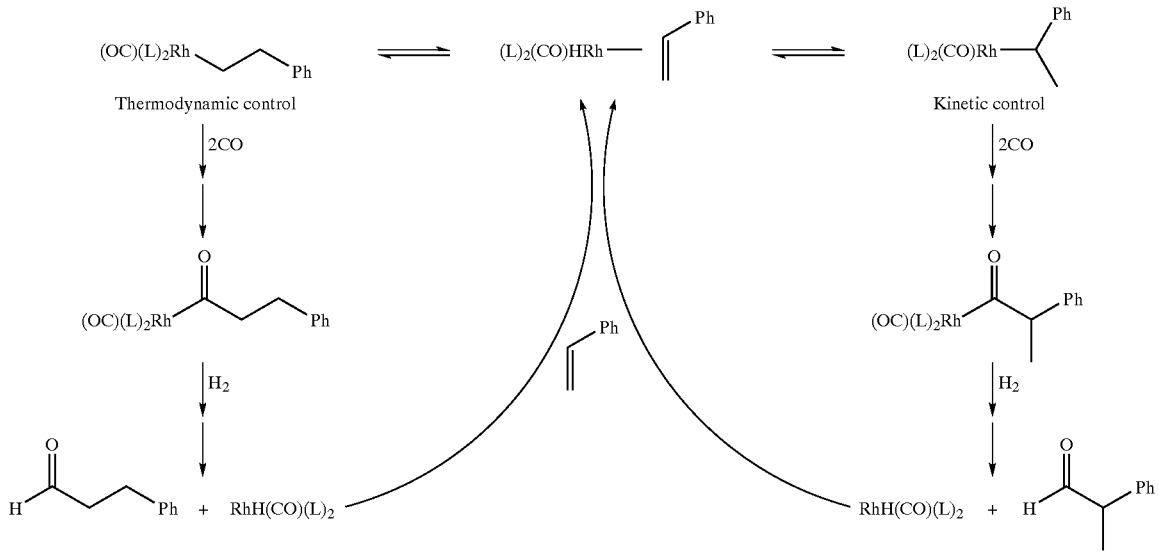

Now CO effectively acts as a 'trapping' agent to form Rh—CO-alkyl species (again both straight and branched alkyl chain) which upon H transfer from Rh, eliminate to form the observed products, 2- and 3-phenylpropanal. Now if the CO 'trapping' is faster or of a comparable rate to the reversible H transfer leading to equilibration of the branched and straight chain Rh-alkyl species, then increasing the CO conc. in solution will favour trapping of the kinetically favoured Rh-alkyl species (apparently the branched Rh-alkyl species) over the thermodynamically favoured straight chain (apparently) Rh-alkyl species. Conversely, 'starving' the solution of CO will favour the formation of increased amounts of product from the thermodynamically favoured straight chain Rh-alkyl species, leading to a lowering of the aldehyde i:n ratio.

The results are summarised in Table 1.

Vinyl Acetate

Optically active aldehydes are very important as precursors not only in biologically active compounds but also for new materials such as biodegradable polymers and liquid crystals. The ESPHOS ligand has demonstrated enormous potential for the asymmetric hydroformylation of vinyl acetate. The chiral branched aldehyde, 2-acetoxypropanal, is a precursor for the Strecker synthesis of the amino acid threonine. The 2-acetoxypropanal product can be converted to 2-hydroxypropanal, a useful intermediate in the synthesis of steroids, pheromones, antibiotics and peptides. Both the ratio of branched to straight chain aldehyde and the enantiomeric excesses obtained using ESPHOS are comparable with the very best results seen in the literature (using BINAPHOS and BIHEMPHOS). That ESPHOS produces virtually racemic product from the hydroformylation of styrene (see below) is somewhat surprising as the ligands BINAPHOS and BIHEMPHOS give large inductions during the hydroformylation of both vinyl acetate and styrene. However, asymmetric induction is usually higher in heterofunctionalised alkenes such as vinyl acetate, presumably due to the additional binding of the C=O bond of the substrate to the catalyst.

The S-(-) enantiomer (authentic synthesis) is the major enantiomer observed for the 2-acetoxypropanal product from ESPHOS catalysed hydroformylations, whereas the slight ee excess observed in one of the SEMI-ESPHOS catalysed hydroformylations is the R enantiomer. The 2-acetoxy-1-propanol (2Ac1ol) arises from sequential hydroformylation of styrene to 2-acetoxypropanal followed by hydrogenation, whereas the 1-acetoxy-2-propanol (1Ac2ol) arises from the isomerisation of 2Ac1ol (primary product) into 1Ac2ol (secondary product). It has also been observed that when the product samples (stored in sealed containers in the dark at room temperature) are re-analysed after a couple of months the 2Ac1ol/1Ac2ol ratio falls considerably relative to that obtained on analysis of a fresh product mixture, presumably eventually reaching an equilibrium ratio. Since the hydrogenation of the aldehyde does not affect the chiral centre we can be sure that the major enantiomer in the 2-acetoxy-1-propanol, arising from ESPHOS catalysed hydroformylation reactions (followed by hydrogenation), is also the S enantiomer. However, various mechanisms can be suggested for the isomerisation of the 2-acetoxy-1-propanol into 1-acetoxy-2-propanol, some of which invert the chiral centre and some which do not, so that we cannot be certain, at this time, which is the major enantiomer in the 1-acetoxy-2-propanol product. However, there are simple methods available which could be used to ascertain which is the major enantiomer for 1-acetoxy-2-propanol. For example, hydrolysis of a product mixture containing high amounts of both 1-acetoxy-2-propanol and 2-acetoxy-1-propanol will give 1,2-propanediol. Now if both the acetoxypropanols are rich in the S enantiomer then (S)-1,2-propanediol will be the major enantiomer, whereas if the 1-acetoxy-2-propanol has been formed through a process which involves inversion of the chiral centre of 2-acetoxy-1-propanol then both the R and S enantiomers will be produced in large amounts.

The acetic acid (AA) will arise from the thermal decomposition of the expected linear aldehyde, 3-acetoxypropanal into propenal (acrolein) and acetic acid.

In the best result, vinyl acetate was hydroformylated employing the ESPHOS/Rh(CO)$_2$ (1:1) for 5 hours, to give 99% conversion with a 90% yield of the branched aldehyde, 2-acetoxypropanal, with 89% ee of the S enantiomer. This result might well be improved upon if conditions of temperature, pressure, CO:H$_2$ ratio and ESPHOS:Rh ratio were optimised. As already stated, this result in terms of ee and i:n ratio of aldehyde is already competitive with the best work in the literature.

Rhodium based catalysts usually give aldehydes as the only products from hydroformylation reactions, especially in aprotic solvents. The formation of some alcohol product may be due to the presence of the acetic acid.

Styrene

Styrene hydroformylation is useful as a model for the asymmetric hydroformylations of vinyl aromatics in general. The hydroformylation reaction of vinyl aromatics lends itself, upon oxidation of the aldehyde, to the synthesis of a number of optically active non-steroidal antiinflammatory agents, 2-arylpropionic acids, for example, (S)-(+)-Ibuprofen, (S)-(+)-Naproxen and Suprofen.

TABLE 1

Asymmetric hydroformylation of alkenes catalysed by rhodium complexes.[a]

| Substrate | Ligand | P:Rh | T/°C | p/bar | t/h | Initial Rate/mol dm-3 s-1 | Conversion/% | VA/% | AA/% | 2Acal/% | 2Acal e.e.(S)/% | 2Ac1ol/% | 2Ac1ol/ e.e.(S)/% | 1Ac2ol/% | 1Ac2ol e.e.(S)/% | AcA/% |
|---|---|---|---|---|---|---|---|---|---|---|---|---|---|---|---|---|
| Vinyl acetate[b] | Esphos | 1.5 | 80 | 40 | 3.0 | 2.2 × 10-3 | 100 | 0 | 5.9 | 34.9 | 76 | 43.0 | 84 | 15.8 | 82 | 0.3 |
| | | 1.5 | 80 | 40 | 1.5 | 3.4 × 10-3 | 98.5 | 1.5 | 7.0 | 37.0 | 84 | 44.3 | 88 | 10.2 | 84 | 0.1 |
| | | 1.5 | 60 | 8 | 3.0 | 2.3 × 10-4 | 80.0 | 20.0 | 5.2 | 74.8 | 90 | 0.6 | — | 0 | 0 | 0 |
| | | 1.5 | 60 | 8 | 5.0 | 2.1 × 10-4 | 98.9 | 1.1 | 5.4 | 90.3 | 89 | 3.3 | — | t | — | t |
| | | 1.5 | 50 | 8 | 21.0 | 7.2 × 10-5 | 98.6 | 1.4 | 5.7 | 75.8 | 88 | 16.0 | 89 | 1.1 | — | t |
| | | 1.5 | 30 | 100 | 17.0 | — | 23.6 | 76.4 | 2.0 | 21.6 | 93 | 0 | — | 0 | — | 0 |
| | Semi-esphose[c] | 3.0 | 80 | 40 | 8.0 | — | 4.2 | 95.8 | 3.1 | 1.1 | — | — | — | — | — | — |
| | | 2.0 | 80 | 40 | 20.0 | — | 10.2 | 89.8 | 7.7 | 2.5 | — | — | — | — | — | — |
| | | 2.0 | 120 | 40 | 6.0 | — | 5.5 | 95.5 | 2.7 | 1.9 | — | — | — | — | — | — |
| | | 2.0 | 120 | 100 | 6.0 | — | 21.8 | 78.2 | 6.0 | 14.7 | <2 | 0.2 | — | 0.3 | — | 0.5 |
| | PPh3 | 3.0 | 80 | 40 | 4.5 | 1.0 × 10-2 | 99.7 | 0.3 | 18.5 | 73.6 | 0 | 1.4 | 0 | 2.7 | 0 | 3.6 |

| Substrate | Ligand | P:RH | T/°C | p/bar | t/h | Inital Rate/mol dm-3 s-1 | Conversion/% | STY/% | ACET/% | 2PhPal/% | 2PhPal/ e.e./% | 3PhPal/% | 2PhPol/% | 3PhPol/% | Other/% |
|---|---|---|---|---|---|---|---|---|---|---|---|---|---|---|---|

TABLE 1-continued

Asymmetric hydroformylation of alkenes catalysed by rhodium complexes.[a]

| Styrene[d] | Esphos | 1.5 | 80 | 10 | 1.5 | 1.0 × 10-3 | 99.6 | 0.4 | 0.7 | 76.9 | 0 | 22.0 | 0 | 0 | 0 |
|---|---|---|---|---|---|---|---|---|---|---|---|---|---|---|---|
| | Semiesphos[e] | 2.0 | 80 | 10 | 2.0 | 1.2 × 10-3 | 91.3 | 8.7 | 2.6 | 51.6 | <1 | 33.4 | 0.4 | 0.7 | 2.7 |
| | PPh3[e] | 3.0 | 80 | 10 | 1.0 | 1.9 × 10-3 | 99.2 | 0.8 | 02 | 54.5 | 0 | 44.6 | 0 | 0 | 0 |

[a]Catalyst preparted in situ from [Rh(2,4-pentanedionato)(CO)$_2$] (5 × 10$^{-3}$ mol) and the phosphine in tolune (4 cm$^2$) containing substrate (1 cm$^3$), autoclave stirring speed = 500 rmp. VA = vinyl acetate; AA = acetic acid; 2Acal = 2-acetoxypropanal; 2Ac1ol = 2-acetoxy-1-propanol; 1Ac2ol = 1-acetoxy-2-propanol; AcA = acetoxyacetone; STY = styrene; ACET = acetophenone; 2PhPal = 2-phenylpropanal; 3PhPal = 3-phenylpropanal; 2PhPol = 2-phenyl-1-propanol; 3PhPol = 3-phenyl-1-propanol.
[b]Acetoxyacetone (0.3–0.6%) is also a product.
[c]Catalyst is unstable.
[d]Acetophenone (<1%) is also a product.
[e]Increasing the stirrer rate to 1000 rpm gives a rate of 3.7 × 10$^{-3}$ and an i:n ratio of 2.8 for the aldehyde.

Asymmetric Hydroformylation

This procedure applies to 2,5-dihydrofuran and 1 atm of carbon monoxide and hydrogen gases, adapted from Nozaki et al, *J. Org. Chem.*, 1997, 62, 4285. A solution of 2,5-dihydrofuran (5 mmol) in benzene (1 ml) is added to a mixture of [Rh(acac)(CO)$_2$] (0.012 mmol) and ligand (0.05 mmol). The reaction vessel is then evacuated and refilled with an equal pressure of hydrogen and carbon monoxide gases to a total pressure of 1 atm. The solution is stirred at 30–40° C. until the reaction is complete, at which point the vessel is vented and the product isolated and characterised by conventional methods. In certain cases it might be necessary to use a higher pressure of hydrogen and CO in which case a steel autoclave would be employed.

Asymmetric Hydrovinylation

To a red solution of [Ni(allyl)Br]$_2$ (0.0072 mmol) in dichloromethane (1.5 ml) is added a solution of ligand (0.014 mmol) in dichloromethane (1.5 ml). The resulting mixture is combined with Na[[3,5]-(CF$_3$)2C$_6$H$_3$]$_4$B] (0.020 mmol) in dichloromethane (2 ml), for 1.5 h. at room temperature and then filtered through a plug of celite. Oxygen free ethylene (1 atm) was introduced and a styrene derivative (1 mmol) added dropwise by syringe at −55° C. The resulting solution is stirred at this temperature until the reaction is complete. After this time the reaction is quenched by the addition of ammonium chloride solution (excess) and the product extracted, dried and the solvent removed to give crude product, which is purified and characterised by conventional methods. (Adapted from supplementary data of Rajanbabu et al, *J. Am. Chem. Soc.*, 1998, 120, 459).

Asymmetric Copolymerisation of Carbon Monoxide and an Alkene

A solution of [Pd(MeCN)$_4$](BF$_4$)$_2$ (0.045 mmol) and ligand (0.045 mmol) in a 2:1 CH3NO2/CH3OH mixture (9 ml) is placed in a steel autoclave or Parr bomb under nitrogen and charged with propylene (30 g) and carbon monoxide (1500 psi). The reaction mixture is stirred at 50° C. for 24 h. during which time the polymeric product precipitates out of the reaction mixture. The precipitation is completed by the addition of further methanol upon venting of the reaction vessel. The product is analysed using conventional methods. Based on Zhang Z. and Sen. A. *J. Am. Chem. Soc.*, 1995, 117, 4455.

Conjugate Addition to Enones

A solution of copper(II)triflate (1 mmol) and ligand (2 mmol) in toluene is stirred for 1 hour at room temperature under nitrogen. The solution is then cooled to ca. −30° C. and enone (100 mmol) and diethylzinc (110 mmol) were added. After 18 hours at −30° C. the reaction is quenched by the addition of excess ammonium chloride solution. The product is extracted with ether, dried and the solvent removed after filtration. The product is purified and characterised by conventional methods. (Adapted from Feringa et al., *Angew. Chem. Int. Ed. Engl.*, 1997, 36, 2620).

Asymmetric Hydrosilylation

This procedure is for alkene hydrosilylation, although it should be equally applicable to ketone hydrosilylation. The ligand (2 mmol) is combined with [PdCl(allyl)]$_2$ (1 mmol), alkene substrate (1000 mmol) and silyl trichloride (1200 mmol). The reaction mixture is stirred until the reaction was complete. The product is purified by direct distillation from the reaction mixture and characterised by conventional methods (adapted from Hayashi et al., *Tetrahedron Lett.*, 1996, 37, 4169).

What is claimed is:

1. A diazaphospholidine compound of Formula 2,

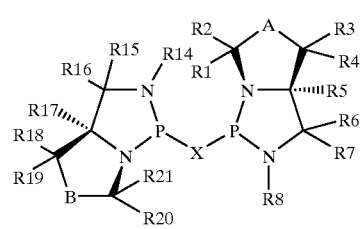

Formula 2 where:

A and B are independently selected from C(R$_{22}$R$_{23}$) and C(R$_{22}$R$_{23}$)C(R$_{24}$R$_{25}$);

R$_1$, R$_2$, R$_3$, R$_4$, R$_{18}$, R$_{19}$, R$_{20}$, R$_{21}$, R$_{22}$, R$_{23}$, R$_{24}$ and R$_{25}$ each may or may not be present and each may be independently selected from H, halide, —OH, —SO$_2$R$_{26}$ (where R$_{26}$ is selected from a group as defined for R$_{22}$, R$_{23}$, R$_{24}$ and R$_{25}$), —SH, —NO$_2$, —NH$_2$, straight chain, branched chain, cyclic, saturated, non-saturated, substituted or non-substituted alkyl, alkoxy, amino, alkenyl, aryl and —CH$_2$ Ar (where Ar is aryl or substituted aryl), a silane containing 1 to 6 silicon atoms, or wherein two groups attached to the same carbon together form an =O or =S, wherein, where an R$_1$, R$_2$, R$_3$, R$_4$, R$_{18}$, R$_{19}$, R$_{20}$, R$_{21}$, R$_{22}$, R$_{23}$, R$_{24}$ and/or R$_{25}$ group is not present an unsaturated bond is formed;

R$_5$ and R$_{17}$ are selected from H, —NH$_2$, —OH, halide or a substituted or non-substituted straight or branched chain alkyl or aryl;

R$_6$, R$_7$, R$_{15}$ and R$_{16}$ are each independently selected from hydrogen, halide, —OH, —SO$_2$, —SH, —NO$_2$, —NH$_2$, straight chain, branched chain, cyclic, saturated, non-saturated, substituted or non-substituted alkyl, alkoxy, alkenyl, aryl and —CH$_2$ Ar (where Ar is aryl or substituted aryl), or a silane containing 1 to 6 silicon atoms;

R$_8$ and R$_{14}$ are selected from H, straight, branched, cyclic, saturated, non-saturated, substituted or non-substituted alkyl, alkoxy, alkenyl, aryl and —CH$_2$ Ar (where Ar is aryl or substituted aryl);

X is a linking group containing 1 to 12 atoms; or a salt thereof.

2. A diazaphospholidine compound according to claim 1, wherein A and B are independently selected from CH$_2$ and (CH$_2$)$_2$.

3. A diazaphospholidine compound according to claim 1, wherein R$_1$, R$_2$, R$_3$, R$_4$, R$_5$, R$_6$, R$_7$, R$_8$, R$_{14}$, R$_{15}$, R$_{16}$, R$_{17}$, R$_{18}$, R$_{19}$, R$_{20}$, R$_{21}$, R$_{22}$, R$_{23}$, R$_{24}$ R$_{25}$ and/or R$_{26}$ independently contain 1 to 6 carbon atoms.

4. A diazaphospholidine compound according to claim 1, wherein R$_1$, R$_2$, R$_3$, and R$_4$ are identical to R$_{21}$, R$_{20}$, R$_{19}$ and R$_{18}$ respectively.

5. A diazaphospholidine compound according to claim 1, wherein R$_5$ and R$_{17}$ are the same.

6. A diazaphospholidine compound according to claim 5, wherein R$_5$ and R$_{17}$ are each H.

7. A diazaphospholidine compound according to claim 1, wherein R$_6$ and R$_7$ are identical to R$_{15}$ and R$_{16}$ respectively.

8. A diazaphospholidine compound according to claim 1, wherein R$_8$ and/or R$_{14}$ are phenyl or substituted phenyl.

9. A diazaphospholidine compound according to claim 1, wherein R$_8$ and R$_{14}$ are identical.

10. A diazaphospholidine compound according to claim 1, wherein x is selected from —S—S—, —O—O—, straight chain, branched chain, cyclic, substituted or non-substituted alkyl, carboalkyl, alkoxy, alkenyl and aryl.

11. A diazaphospholidine compound according to claim 1, of Formula 4:

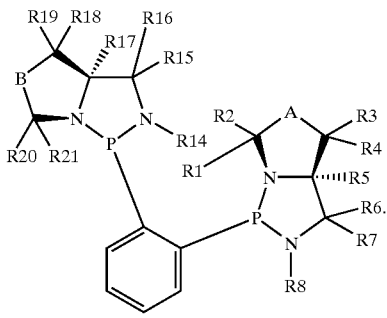

Formula 4

12. A diazaphospholidine compound according to claim 11 of Formula 5:

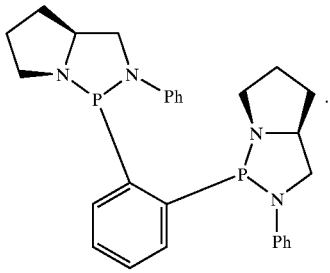

Formula 5

13. A diazaphospholidine compound according to claim 1, chelated to at least one transition metal ion.

14. A diazaphospholidine compound according to claim 13, wherein the transition metal is selected from palladium, ruthenium, rhodium, tungsten, nickel, platinum, copper, cobalt, zinc and molybdenum.

15. A chemical formulation or composition comprising a diazaphospholidine compound according to claim 1.

16. A diazaphospholidine compound according to claim 1, chelated to a transition metal to form a catalyst.

17. A process for carrying out an organic asymmetric catalysis reaction selected from the group consisting of: asymmetric hydrogenation, asymmetric allylic substitution, asymmetric hydroformylation, asymmetric hydrovinylation, asymmetric copolymerisation, asymmetric conjugate addition and asymmetric hydrosilylation, said process comprising reacting two or more suitable reactants in the presence of a catalyst comprising a transition metal and a diazaphospholidine compound according to claim 1.

18. A process according to claim 17, wherein the organic asymmetric catalysis reaction is asymmetric hydrogenation.

19. A process according to claim 17, wherein the transition metal is rhodium.

20. A process according to claim 17, wherein the organic asymmetric catalysis reaction is asymmetric hydroformylation.

21. Process according to claim 20, wherein the diazaphospholidine compound is as defined in claim 12.

22. Process according to claim 20 wherein the transition metal is rhodium.

23. Process according to claim 17, wherein the organic asymmetric catalysis reaction is asymmetric hydrovinylation.

24. Process according to claim 23, wherein the transition metal is nickel.

25. Process according to claim 17, wherein the organic asymmetric catalysis reaction is asymmetric copolymerisation.

26. Process according to claim 25, wherein the transition metal is palladium.

27. Process according to claim 17, wherein the organic asymmetric catalysis reaction is a conjugate addition reaction.

28. Process according to claim 17, wherein the organic asymmetric catalysis reaction is asymmetric hydrosilylation.

29. Process according to claim 28, wherein the transition metal is palladium or rhodium.

30. A process for the production of a diazaphospholidine compound of Formula 2:

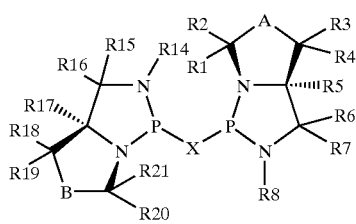

Formula 2 as defined in claim 1, comprising the steps of:

a) providing a compound having a formula:

X(P(NMe$_2$)$_2$)$_2$ where X is as defined in claim 1, b) mixing with a compound of Formula 7;

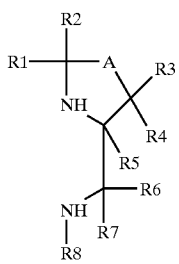

Formula 7 where:
- A is independently selected from $C(R_{22}R_{23})$ and $C(R_{22}R_{23})C(R_{24}R_{25})$;
- $R_1$, $R_2$, $R_3$, $R_4$, $R_{22}$, $R_{24}$ and $R_{25}$ each may or may not be present and each may be independently selected from H, halide, —OH, —SO$_2$R$_{26}$ (where $R_{26}$ is selected from a group as defined for $R_{22}$, $R_{23}$, $R_{24}$ and $R_{25}$), —SH, —NO$_2$, —NH$_2$, straight chain, branched chain, cyclic, saturated, non-saturated, substituted or non-substituted alkyl, alkoxy, amino, alkenyl, aryl and —CH$_2$Ar (where Ar is aryl or substituted aryl), a silane containing 1 to 6 silicon atoms, or wherein two groups attached to the same carbon together form an =O or =S,
- wherein, where an $R_1$, $R_2$, $R_3$, $R_4$, $R_{22}$, $R_{23}$, $R_{24}$ and/or $R_{25}$ group is not present an unsaturated bond is formed;
- $R_5$ is selected from H, —NH$_2$, —OH, halide or a substituted or non-substituted straight or branched chain alkyl or aryl;
- $R_6$ and $R_7$ are each independently selected from hydrogen, halide, —OH, —SO$_2$, —SH, —NO$_2$, —NH$_2$, straight chain, branched chain, cyclic, saturated, non-saturated, substituted or non-substituted alkyl, alkoxy, alkenyl, aryl and —CH$_2$Ar (where Ar is aryl or substituted aryl), or a silane containing 1 to 6 silicon atoms;
- $R_8$ is selected from H, straight, branched, cyclic, saturated, non-saturated, substituted or non-substituted alkyl, alkoxy, alkenyl, aryl and —CH$_2$Ar (where Ar is aryl or substituted aryl);
- X is a linking group containing 1 to 12 atoms;

or a salt thereof;

and c) heating.

31. A process according to claim 30, wherein the compound in step (a) has Formula 8:

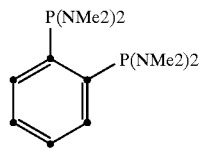

Formula 8

32. A diazaphospholidine compound represented by Formula 5:

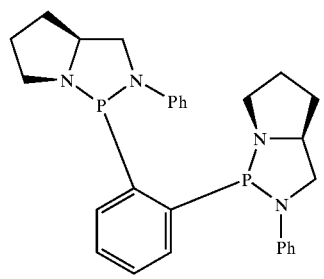

Formula 5

33. A process for carrying out an organic asymmetric hydroformylation catalysis reaction, said process comprising reacting two or mare suitable reactants in the presence of a catalyst comprising a transition metal and a diazaphospholidine compound according to claim 32.

* * * * *